(12) United States Patent
Kolluri et al.

(10) Patent No.: US 6,893,403 B2
(45) Date of Patent: May 17, 2005

(54) OSCILLOMETRIC DETERMINATION OF BLOOD PRESSURE

(75) Inventors: Sai Kolluri, Tampa, FL (US); Lawrence T. Hersh, Tampa, FL (US); Richard Medero, Tampa, FL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 66 days.

(21) Appl. No.: 10/374,240

(22) Filed: Feb. 25, 2003

(65) Prior Publication Data

US 2004/0167411 A1 Aug. 26, 2004

(51) Int. Cl.[7] .................................................. A61B 5/00
(52) U.S. Cl. ....................................... 600/494; 600/496
(58) Field of Search .......................... 600/490, 493–496

(56) References Cited

U.S. PATENT DOCUMENTS

| | | | |
|---|---|---|---|
| 4,360,029 A | 11/1982 | Ramsey, III | 128/681 |
| 4,543,962 A | 10/1985 | Medero et al. | 128/682 |
| 4,638,810 A | 1/1987 | Ramsey, III et al. | 128/681 |
| 4,729,383 A * | 3/1988 | Susi | 600/494 |
| 4,796,184 A | 1/1989 | Bahr et al. | 364/413.03 |
| 4,889,133 A | 12/1989 | Nelson et al. | 128/681 |
| 4,949,710 A | 8/1990 | Dorsett et al. | 128/680 |
| 5,054,494 A * | 10/1991 | Lazzaro et al. | 600/490 |
| 5,505,206 A * | 4/1996 | Walloch | 600/494 |
| 5,542,428 A * | 8/1996 | Jayne | 600/494 |
| 5,579,776 A | 12/1996 | Medero | 128/680 |
| 5,590,662 A * | 1/1997 | Hersh et al. | 600/494 |
| 5,704,362 A | 1/1998 | Hersh et al. | 128/680 |
| 6,358,213 B1 * | 3/2002 | Friedman et al. | 600/493 |
| 6,423,010 B1 | 7/2002 | Friedman et al. | 600/494 |
| 6,440,080 B1 | 8/2002 | Booth et al. | 600/494 |
| 2002/0082507 A1 | 6/2002 | Kolluri et al. | |

* cited by examiner

*Primary Examiner*—Robert L. Nasser
(74) *Attorney, Agent, or Firm*—Andrus, Sceales, Starke & Sawall, LLP (57) ABSTRACT

A method and system for eliminating artifacts in an oscillation envelope are disclosed. The method and system comprise evaluating conformance of the oscillometric envelope blood pressure data with a predetermined expected pattern and excluding one or more data points of the oscillometric envelope blood pressure data based on non-conformance with the expected pattern. The expected pattern is based upon generally known physiological principles relating to oscillometric envelopes, a curve fit representing an oscillometric envelope from a previous determination, or other types of criteria.

11 Claims, 12 Drawing Sheets

OSCILLOMETRIC DETERMINATION OF BLOOD PRESSURE

BACKGROUND OF THE INVENTION

The field of the invention is patient monitoring systems. More particularly, the invention relates to an improved patient monitoring method and system using pattern recognition techniques to eliminate noise points in an oscillometric envelope.

The heart muscles of humans periodically contract to force blood through the arteries. As a result of this pumping action, pressure pulses or oscillations exist in these arteries and cause them to cyclically change volume. The baseline pressure for these pulses is known as the diastolic pressure and the peak pressure for these pulses is known as the systolic pressure. A further pressure value, known as the "mean arterial pressure" (MAP), represents a time-weighted average of the blood pressure.

There are different techniques and devices for measuring one or more of these blood pressure values. One method in particular involves applying a pressure cuff about the upper arm of a human and inflating it above systolic pressure so as to restrict the flow of blood in the brachial artery. The pressure is then slowly relieved while a stethoscope is used on the distal portion of the artery to listen for pulsating sounds, known as Korotkoff sounds, that accompany the reestablishment of blood flow in the artery. As the pressure in the cuff is reduced further, the Korotkoff sounds eventually disappear. The cuff pressure at which the Korotkoff sounds first appear during deflation of the cuff is an indirect measure of the systolic pressure and the pressure at which these sounds disappear is an indirect measure of the diastolic pressure. This method of blood pressure detection is generally known as the auscultatory method.

Another method of measuring blood pressure is referred to as the oscillometric technique. This method of measuring blood pressure involves applying an inflatable cuff around an extremity of a patient's body, such as the patient's upper arm. The cuff is then inflated to a pressure above the patient's systolic pressure and then incrementally reduced in a series of small steps (or continuously at a substantially constant rate). A pressure sensor measures the cuff pressure throughout the blood pressure determination. The sensitivity of the sensor is such that pressure fluctuations within the cuff resulting from the beats of the patient's heart may be detected. With each beat there is a resulting small change in the artery volume which is transferred to the inflated cuff causing slight pressure variations within the cuff which are detected by the pressure sensor. The pressure sensor produces an electrical signal showing the incremental cuff pressure and a series of small periodic variations associated with the beats of a patient's heart. It has been found that these variations, called "complexes" or "oscillations," have a peak-to-peak amplitude which is minimal for applied cuff pressures above the systolic pressure. As the cuff pressure is decreased, the oscillation size begins to monotonically grow and eventually reaches a maximum amplitude. After the oscillation size reaches the maximum amplitude, the oscillation size decreases monotonically as the cuff pressure continues to decrease. Oscillometric envelope data such as this is often described to as having a "bell curve" appearance. Physiologically, the cuff pressure at the maximum value approximates the MAP. In addition, the complex amplitudes of cuff pressures equivalent to the systolic and diastolic pressures have a fixed relationship to this maximum value. Thus, the oscillometric method is based on measurements of detected complex amplitudes at various cuff pressures.

Blood pressure measuring devices operating according to the oscillometric method detect the peak-to-peak amplitude of the pressure complexes at the various applied cuff pressure levels. The amplitudes of these complexes, as well as the applied cuff pressure, are stored together as the device automatically changes the cuff pressures over a range of interest. These peak-to-peak complex amplitudes define an oscillometric "envelope" and are evaluated to find the maximum value and its related cuff pressure, which is approximately equal to MAP. The cuff pressure below the MAP value which produces a peak-to-peak complex amplitude having a certain fixed relationship to the maximum value is designated as the diastolic pressure. Likewise, the cuff pressure above the MAP value which results in complexes having an amplitude with a certain fixed relationship to that maximum value is designated as the systolic pressure. The relationships of complex amplitude at systolic and diastolic pressures, respectively, to the maximum value, are empirically derived ratios which assume varying levels depending on the preferences of those of ordinary skill in the art. Generally, these ratios are designated in the range of 40% to 80%.

One way to determine oscillation magnitudes is to computationally fit a curve to the oscillometric envelope defined by complex amplitude data points which are measured by a blood pressure monitor at varying cuff pressures. The fitted curve may then be used to compute an approximation of the MAP data point, which is approximately at the maximum value of the fitted curve and is therefore easily determined by computing the point on the fitted curve in which the first derivative equals zero. From this maximum value data point, the systolic and diastolic pressures may be computed as fixed percentages of the maximum value. In this manner, the systolic data point and the diastolic data point along the fitted curve may each be computed and therefore their respective pressures may also be determined. This curve fitting technique has the advantage of filtering or smoothing the oscillometric envelope. However, in some circumstances it has been found that additional filtering techniques used on the oscillometric envelope can improve the accuracy of the resulting blood pressure values.

The reliability and repeatability of blood pressure computations hinges on the ability to accurately determine the oscillation magnitudes of the complexes. There are several barriers to accurate and reliable oscillation magnitude determination. First, artifacts caused by patient motion and other effects are often present. These artifacts are superimposed upon the desired oscillation signal, causing it to be distorted. Second, many of the properties of the desired oscillation signal are not consistent from patient to patient, or even from oscillation to oscillation for a given patient. Because of these types of potentially adverse effects on the oscillometric signals, most automatic blood pressure instruments look for a consistency in pulses at a particular pressure level. For example, before a complex is accepted as adequate for use in the determination of blood pressure, there may be a requirement for consistency in pulse size compared to other pulses at the same step, adjacent steps, or previous determinations at the same pressure level. Further, there may be requirements on the consistency of pulse periods before a pulse is accepted as adequate for use in a blood pressure determination.

Despite significant signal processing efforts, artifact corrupted complexes are sometimes used in blood pressure calculations. Oftentimes, these complexes are of such an energy level that they unduly influence the curve fit smoothing technique. Thus, there exists a need for a method and system for effectively using pattern recognition techniques to eliminate noise or physiologically unimportant points in oscillometric envelope data before it is used in calculating blood pressure.

SUMMARY OF THE INVENTION

One embodiment of the present invention provides a method of rejecting artifacts in oscillometric envelope blood pressure data including evaluating conformance of the oscillometric envelope blood pressure data with a predetermined expected pattern. In addition, the method includes excluding one or more data points of the oscillometric envelope blood pressure data based on non-conformance with the expected pattern.

Another embodiment of the present invention provides a method of rejecting artifacts in oscillometric envelope blood pressure data including evaluating conformance of the oscillometric envelope blood pressure data with previous blood pressure data that meets acquisition time requirements. In addition, the method includes excluding one or more data points of the oscillometric envelope blood pressure data based on non-conformance with the previous blood pressure data.

Another embodiment of the present invention provides a method of rejecting artifacts in oscillometric envelope data including storing data for a plurality of blood pressure data points, including acquisition time. In addition, the method includes removing a blood pressure data point having an earliest acquisition time from the oscillometric envelope blood pressure data and reacquiring the data.

Another embodiment of the present invention provides a method of rejecting artifacts in oscillometric envelope data including applying a curvefit to the oscillometric envelope blood pressure data, measuring a quality of deviation of the oscillometric envelope blood pressure data from the curvefit and comparing the quality of deviation of the oscillometric envelope blood pressure data to an allowed threshold. In addition, the method includes removing a data point where the quality of deviation for that data point exceeds the allowed threshold.

Another embodiment of the present invention provides an apparatus for measuring blood pressure including an inflatable cuff, a pressurizing apparatus, a cuff pressure sensor, and a programmed control device. The pressurizing apparatus is coupled to the cuff for selectively applying pressure by inflating or deflating the cuff. The cuff pressure sensor is coupled to the cuff for sensing cuff pressure and blood pressure oscillations. Further, the programmed control device functions to control the pressure cuff and pressurizing apparatus, evaluate conformance of the blood pressure oscillations with a predetermined expected pattern, and exclude one or more data points of the blood pressure oscillations based on non-conformance with the expected pattern.

Another embodiment of the present invention provides a system for rejecting artifacts in oscillometric envelope blood pressure data including a means for evaluating conformance of the oscillometric envelope blood pressure data with a predetermined expected pattern and a means for excluding one or more data points of the oscillometric envelope blood pressure data based on non-conformance with the expected pattern.

Another embodiment of the present invention provides a computer program product including a computer useable medium having computer logic for enabling at least one processor in a computer system to reject artifacts in oscillometric envelope blood pressure data. In addition, the computer program product includes a means for evaluating conformance of the oscillometric envelope blood pressure data with a predetermined expected pattern and a means for excluding one or more data points of the oscillometric envelope blood pressure data based on non-conformance with the expected pattern.

DESCRIPTION OF THE PREFERRED EMBODIMENT

Figure 1A:
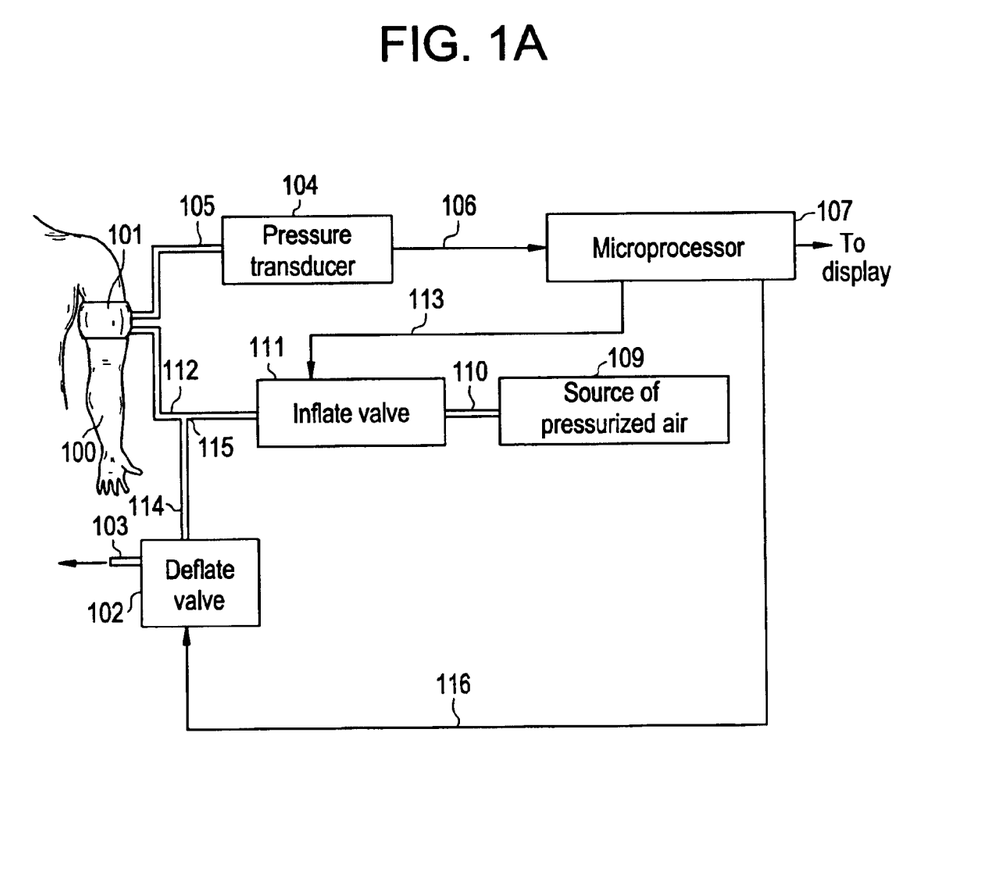
FIG. 1A is a diagram of a non-invasive blood pressure monitoring system in accordance with an embodiment of the present invention.

FIG. 1A shows the arm of a human subject wearing a conventional flexible inflatable and deflatable cuff 101 of occluding the brachial artery when fully inflated. As cuff 101 is deflated using deflate valve 102 having exhaust 103, the arterial occlusion is gradually relieved. The deflation of cuff 101 via deflate valve 102 is controlled by microprocessor 107 via control line 116.

A pressure transducer 104 is coupled by a tube or duct 105 to the cuff 101 for sensing the pressure therein. In accordance with conventional oscillometric techniques, pressure oscillations in the artery are sensed by changes in the counter-pressure of the cuff 101, and these pressure oscillations are converted into an electrical signal by transducer 104 and coupled over path 106 to microprocessor 107 for processing. In addition, a source of pressurized air 109 is connected via a duct 110 through an inflate valve 111 and a duct 112 to the pressure cuff 101. The inflate valve 111 is electrically controlled through a connection 113 from the microprocessor 107. Also, the deflate valve 102 is connected by duct 114 via a branch connection 115 with the duct 112 leading to cuff 101.

Figure 1B:
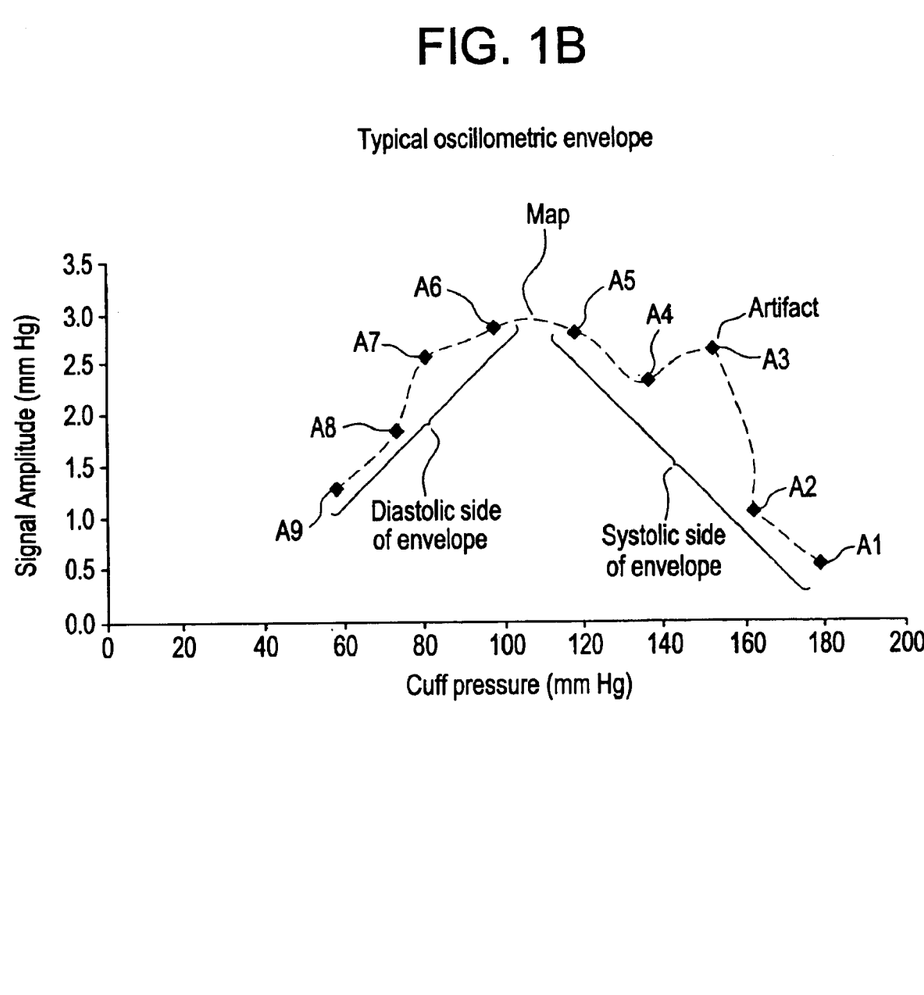
FIG. 1B is a typical oscillometric envelope derived during a non-invasive blood pressure determination.

FIG. 1B shows a typical oscillometric envelope derived during a non-invasive blood pressure determination. The oscillometric envelope is created by plotting complex amplitudes (mm Hg) at various cuff pressures (mm Hg). Point A1 represents a first data point in a descending order of pressure steps (i.e., A2 is a second data point, A3 is a third data point, etc.). For this set of points, the MAP would be between points A5 and A6. The systolic side of the envelope occurs on the higher cuff pressure side of the MAP whereas the diastolic side of the envelope occurs on the lower pressure side of the MAP. As discussed in this specification, point A3 represents an artifact.

Figure 1C:
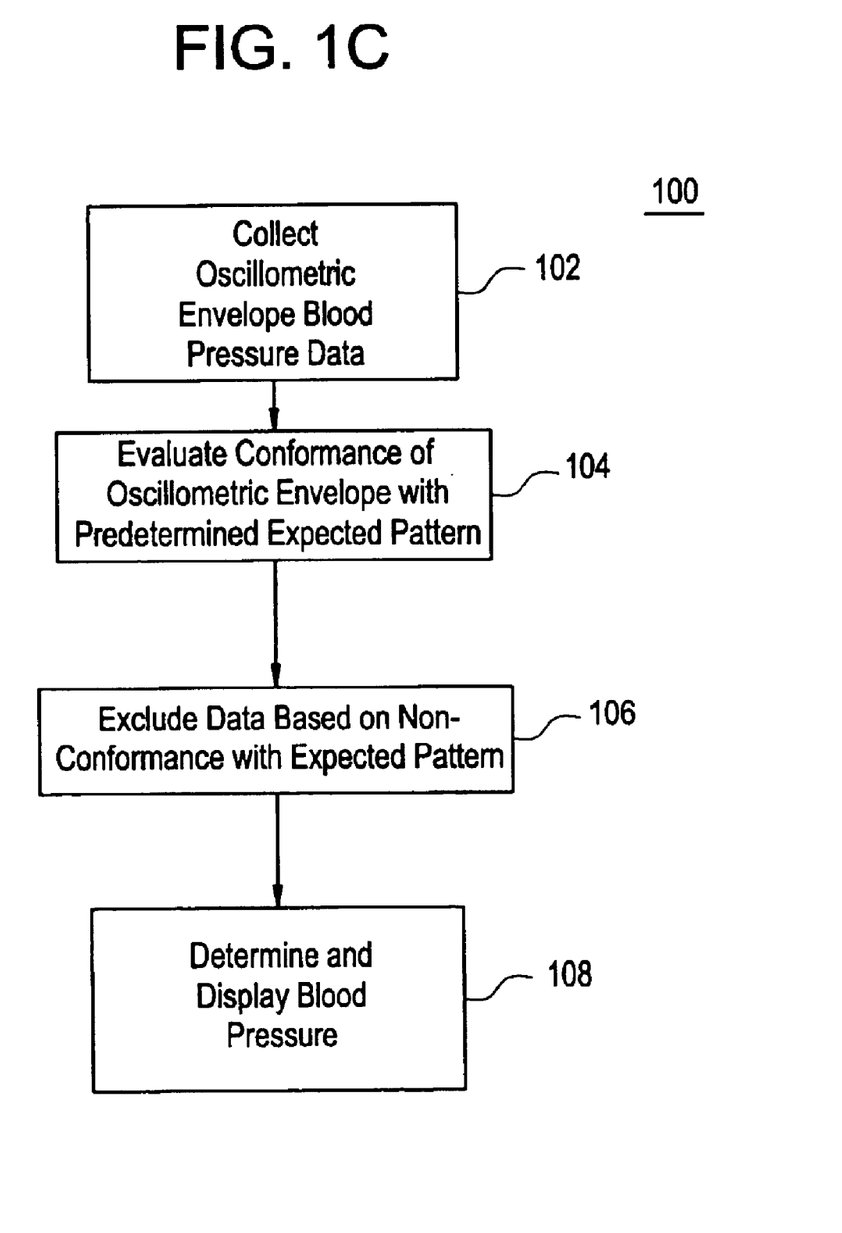
FIG. 1C is a flow chart of a process of rejecting artifacts in oscillometric envelope blood pressure data according to an embodiment of the present invention.

FIG. 1C shows a general process for eliminating artifacts in an oscillation envelope. Oscillometric envelope blood pressure data is collected at step 102. The conformance of the oscillometric envelope blood pressure data is evaluated with a predetermined expected pattern at step 104. In addition, one or more points of the oscillometric envelope blood pressure data may be excluded or removed based on non-conformance with the expected pattern at step 106. Further, the blood pressure may be determined and displayed at step 108. One general expectation in the pattern of the oscillometric envelope is that the complex size monotonically increases on the systolic side as cuff pressure decreases and complex size monotonically decreases on the diastolic side as cuff pressure decreases. Therefore, the identification of local maxima and minima in the oscillometric envelope data sorted by decreasing cuff pressure may help identify artifact or physiologically unimportant points.

Figure 2:
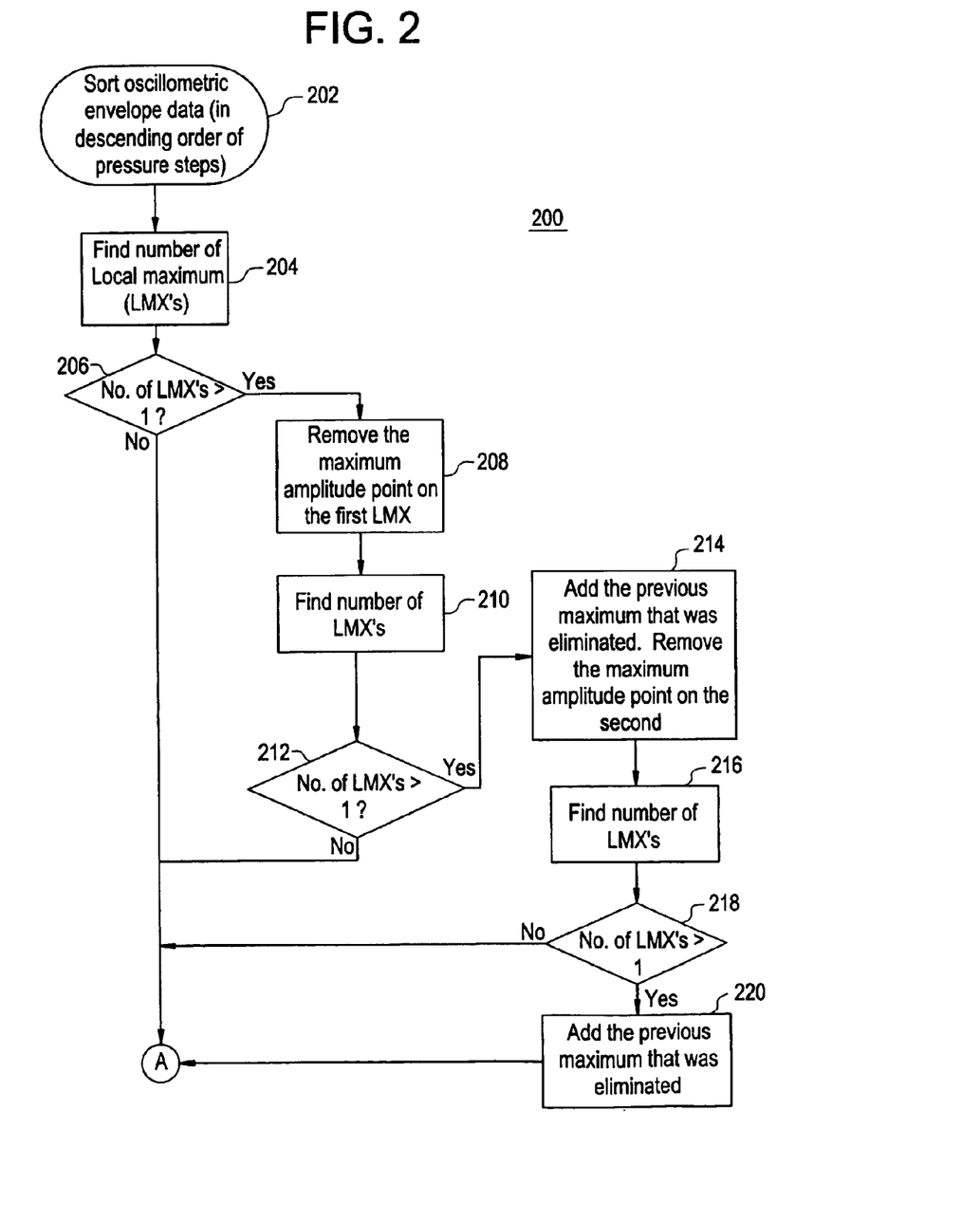
FIG. 2 is a flow chart of a portion of the process of eliminating noise or physiologically unimportant points in an oscillometric envelope according to an embodiment of the present invention.

FIG. 2 shows a portion of a process for removing extraneous data points from an oscillometric envelope based on pattern recognition techniques. Process 200 provides a method of rejecting artifacts in an oscillometric envelope by evaluating conformance of the envelope data with a predetermined expected pattern and excluding one or more data points based on non-conformance with the expected pattern. The first step of the process is to sort the oscillometric envelope data in descending order of pressure steps at step 202. Once the data is sorted, the number of local maxima is determined at step 204. A principle typically used is that a good physiological oscillometric envelope should have only one maxima. The oscillometric data is examined by the technique shown in FIG. 6 (described later) to see if, in the case of an envelope with multiple local maxima, the removal of one local maxima will result in a physiologically proper envelope. If the removal of only one local maxima provides the expected envelope pattern, then that local maxima is very likely an artifact, and removing it will usually result in a more accurate blood pressure estimation.

Local maxima are indicated by points that create significant vertexes, apexes, humps, peaks, rises, etc. on the oscillometric envelope relative to the other data points. They typically can be determined mathematically or through other similar methods. At step 206, it is determined whether the number of local maxima is greater than one. If the number is greater than one, then the maximum amplitude point on the first local maxima (closer to the systolic side of the envelope) is removed at step 208. Then, the number of local maxima is once again determined at step 210. If the number of local maxima is greater than one at step 212, then the previous maximum amplitude point that was removed at step 208 is added back into the data at step 214. In addition, the maximum amplitude point on the second local maxima is removed at step 214. Once the point is removed, the number of local maxima is once again determined at step 216. If the number is greater than one at step 218, the previous maxima that was eliminated is added back to the data at step 220. If the number of local maxima is not greater than one at steps 206, 212, 218, then the process for removing extraneous data points from the oscillometric envelope based on pattern recognition techniques proceeds to the process shown in FIG. 3.

It should be noted that each of the steps described above with regard to FIG. 2 are applicable to local minima as well as local maxima. Local minima include points that create significant indentations, recesses, valleys, dips, depressions, bottoms, etc. on the oscillometric envelope relative to the other data points. For example, instead of finding the number of local maxima at step 204, the number of local minima may be found. In addition, if the number of local minima is greater than a particular threshold at step 206, then the minimum amplitude point on the first local minima is removed at step 208. Since both local maxima and local minima are oftentimes equally applicable in various situations, the term local extreme will sometimes be used in this application to generically refer to both local maxima and local minima.

Figure 3:
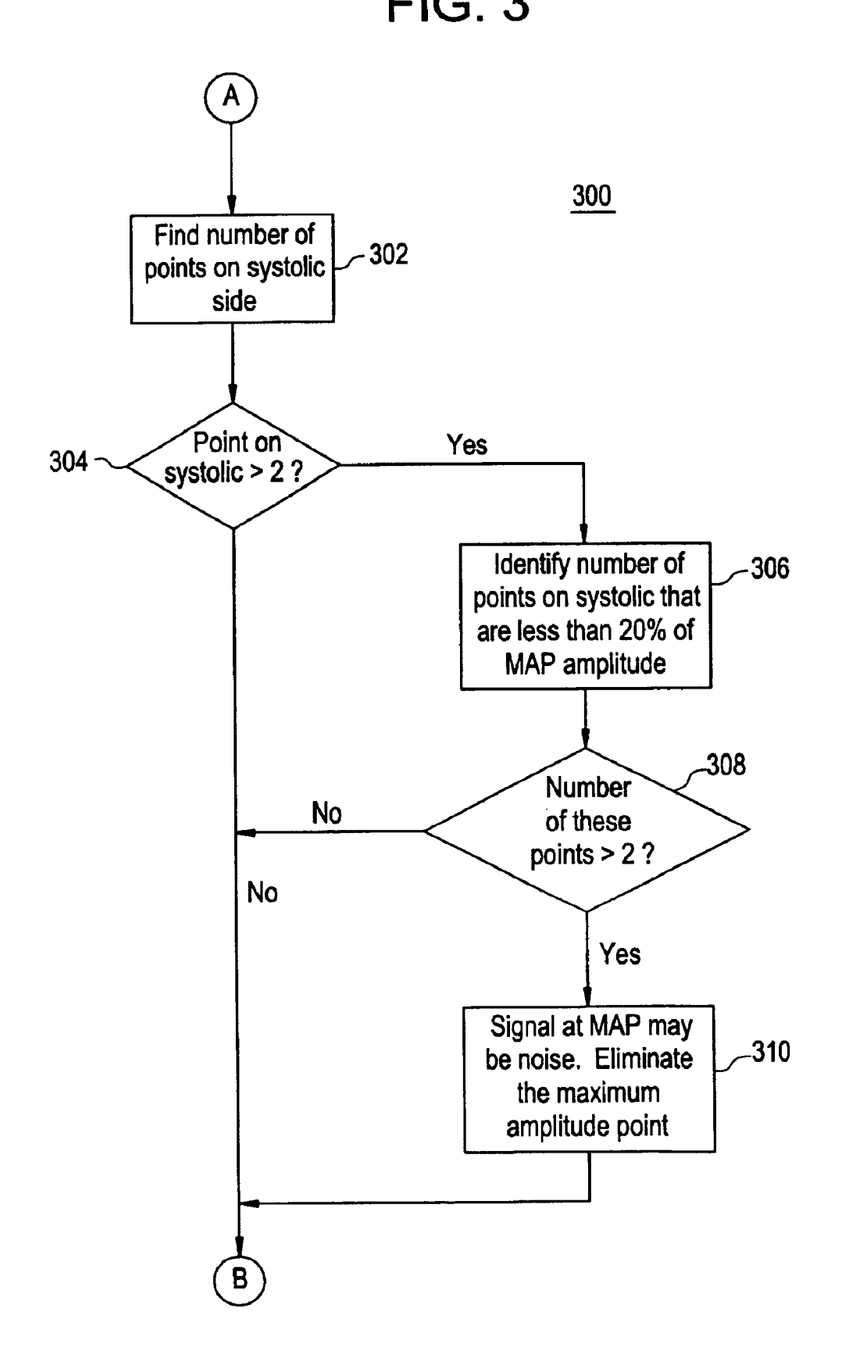
FIG. 3 is a flow chart of a portion of the process of eliminating noise or physiologically unimportant points in an oscillometric envelope according to an embodiment of the present invention.

Referring to FIG. 3, process 300 provides additional methods of eliminating noise or physiologically unimportant points from envelope data based on expected patterns for the oscillometric envelope curve. When examining the oscillometric data for possible use with a curve fitting technique to calculate blood pressure, it is important to have enough envelope points on each side of the maxima (i.e., MAP) in order to capture the true envelope shape. Experience has shown that a minimum number of points are required to adequately find the proper shapes on both the systolic and diastolic sides. However, at the same time it is important to not include points that do not add useful information and may cause the curve fitting optimization process to be biased. FIG. 3 shows a technique for making a fairer distribution of envelope data used in the curve fit process so that blood pressure can be accurately calculated.

Process 300 begins by finding the number of points on the systolic side of the data at step 302. At step 304, the process determines whether the number of points on the systolic side of the data is greater than two. If the number is greater than two, the process identifies the number of points on the systolic side that are less than 20% of the MAP amplitude at step 306. While this example uses the value equal to 20% of the MAP amplitude, other values may be used. For example, values that are close to 20% (e.g., 15% 18%, 23%, 25%, etc.) may also be used. At step 308, the process determines whether the number of these points is greater than two. If so, it is possible that the signal at the MAP may be noise since it is unlikely that a large number of the systolic data points are less than 20% of the MAP. Consequently, the maximum amplitude point is eliminated from the data at step 310. However, if the number of points at steps 304 and 308 are not greater than two, the process for removing data points from oscillometric envelopes proceeds to FIG. 4A.

Figure 4A:
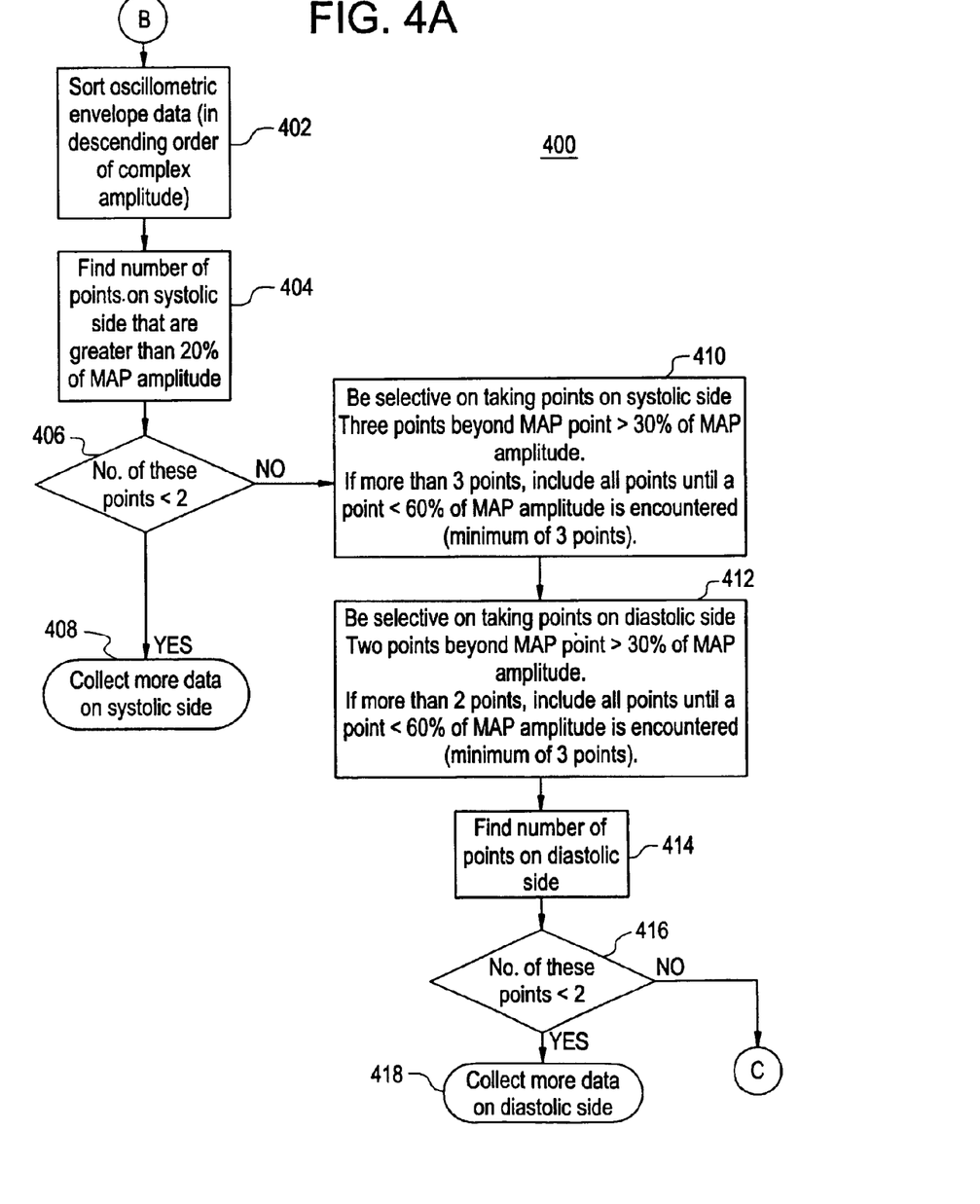
FIG. 4A is a flow chart of a portion of the process of eliminating noise or physiologically unimportant points in an oscillometric envelope according to an embodiment of the present invention.

Referring to FIG. 4A, process 400 provides further methods of eliminating noise points from envelope data based on expected patterns for an oscillometric envelope curve. Process 400 begins by organizing (i.e., categorizing, sorting, etc.) the oscillometric envelope data in descending order of complex amplitude at step 402. The number of points on the systolic side that are greater than 20% of MAP amplitude is determined at step 404. Of course, the use of particular percentages in this example is merely exemplary and a variety of similar values may also be used in their place in order to obtain a desired result. Step 406 analyzes whether the number of points greater than 20% of the MAP on the systolic side is less than two. If the number of points from step 406 is less than two, more data on the systolic side is collected at step 408 and the entire evaluation process is repeated after collecting new data. If the number of points from step 406 is equal to two or more, points are selectively obtained for blood pressure calculations from the systolic side at step 410, including up to three points that are greater than 30% of the MAP amplitude, at least one of which must be less than 60% of the MAP amplitude.

If the number of points from step 406 is equal to two or more, points are also selectively obtained from the diastolic side at step 412 by including two points that are greater than 30% of the MAP amplitude. At least one point should be included that is less than 60% of the MAP amplitude at step 412. After the points are taken out of the data at steps 410, 412, the number of points on the diastolic side are determined at step 414. Whether the number of points on the diastolic side is less than two is determined at step 416. If the number of points is less than two, more data is collected on the diastolic side at step 418 and the entire evaluation process is repeated. If the number of points is equal to two or more, the algorithm proceeds to FIG. 5.

Figure 4B:
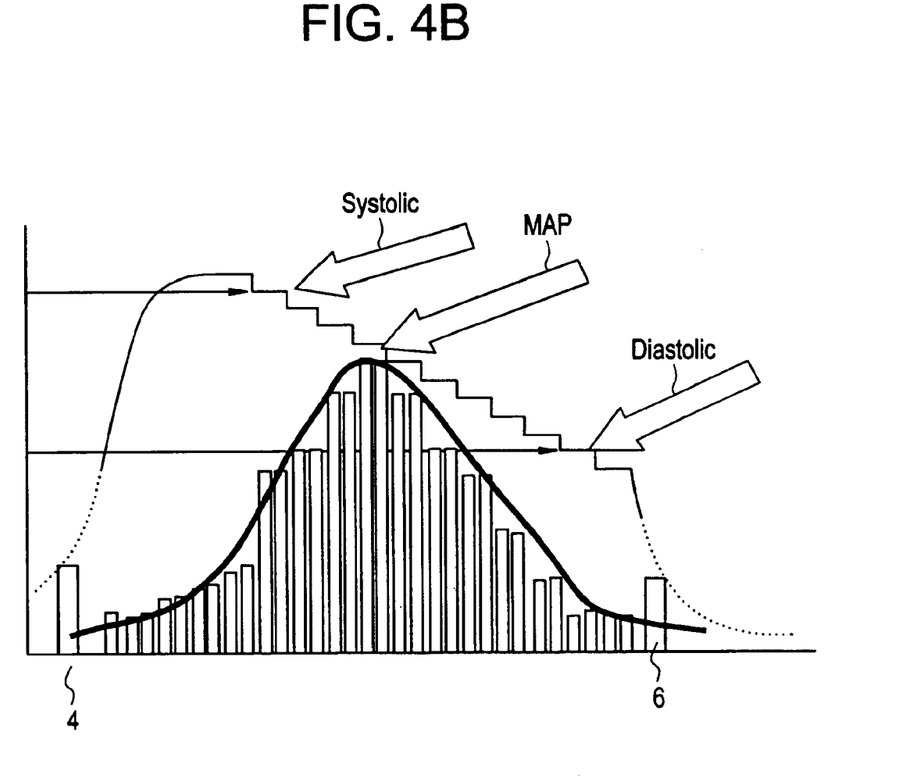
FIG. 4B is a diagram of an oscillometric envelope showing large complexes after the minimum complexes on the diastolic and systolic ends of the envelope.
Figure 5:
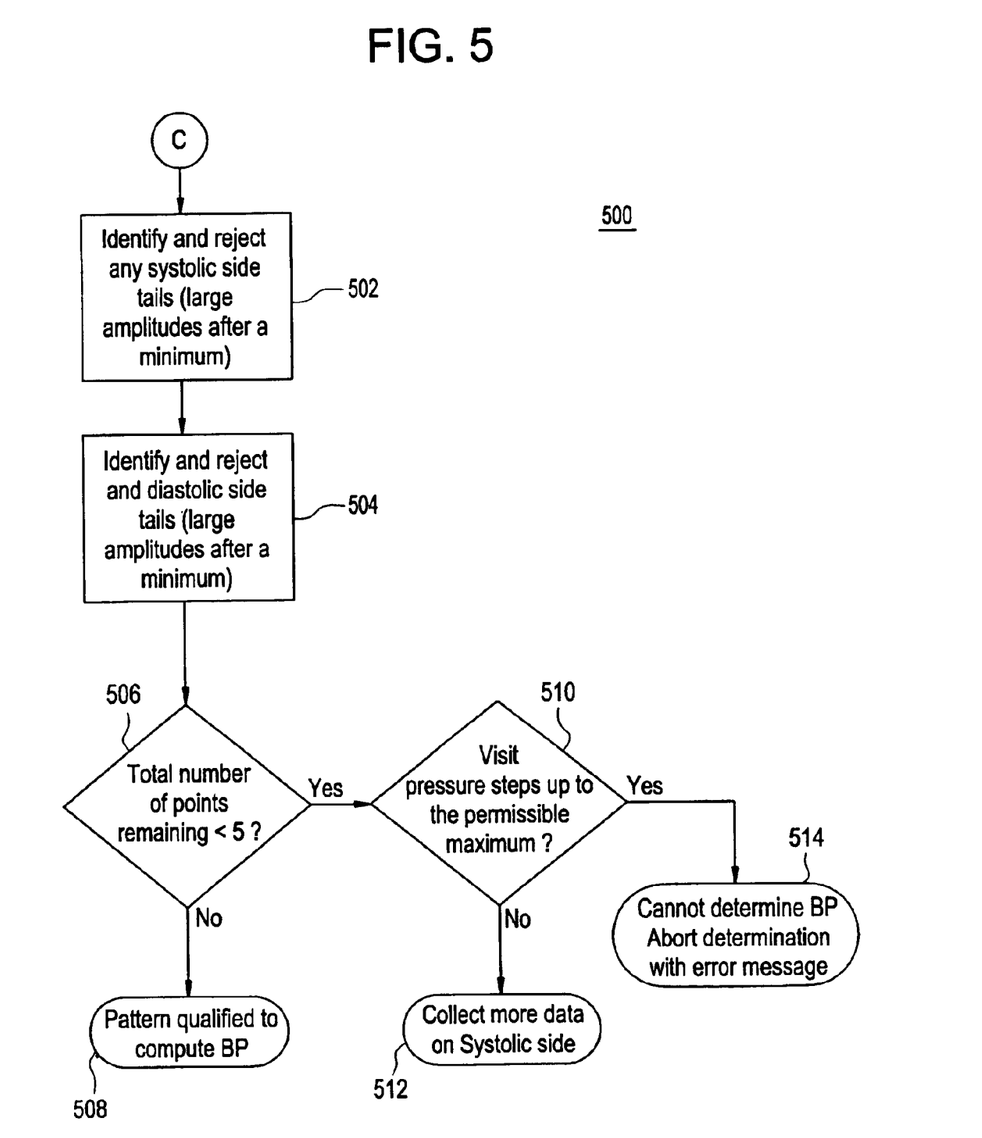
FIG. 5 is a flow chart of a portion of the process of eliminating noise or physiologically unimportant points in an oscillometric envelope according to an embodiment of the present invention.

Referring to FIG. 5, process 500 provides further methods of eliminating noise points from envelope data based on expected patterns for the oscillometric envelope curve. Process 500 begins by identifying and rejecting any systolic side tails. These are generally characterized as large amplitudes after the oscillometric envelope has dropped below a minimum. FIG. 4B shows an example of a systolic side tail 4 and a diastolic side tail 6. Physiologically, it is generally known in the art that the oscillometric envelope cannot have rises in complex amplitude as cuff pressure moves away from the MAP value. Therefore, it is important to remove these tails so that they do not incorrectly influence the calculation of blood pressure when using curve fit techniques. A curve may be computed using a variety of known techniques. One example of such a technique of computationally fitting a curve to an oscillometric envelope is disclosed in U.S. Pat. No. 5,704,362 to Hersh et al. Similarly, the algorithm identifies and rejects any diastolic side tails at step 504. These are also characterized as large amplitudes after the oscillometric envelope has dropped below a minimum. Whether or not the total number of points remaining after step 506 is less than 5 is determined at step 506. If the total number of points remaining is equal to five or more, the pattern qualifies for computing blood pressure at step 508. If the total number of points remaining is less than five, the question of whether enough pressure steps up to the permissible maxima were visited is analyzed at step 510. For adult patients, the permissible maxima is about 300 mm Hg. For neonatal patients, the permissible maxima is about 150 mm Hg. If there have not been enough pressure steps visited, more data is collected on the systolic side at step 512 and the entire process is repeated. Otherwise, the blood pressure cannot be determined and the determination is aborted at step 514.

Figure 6:
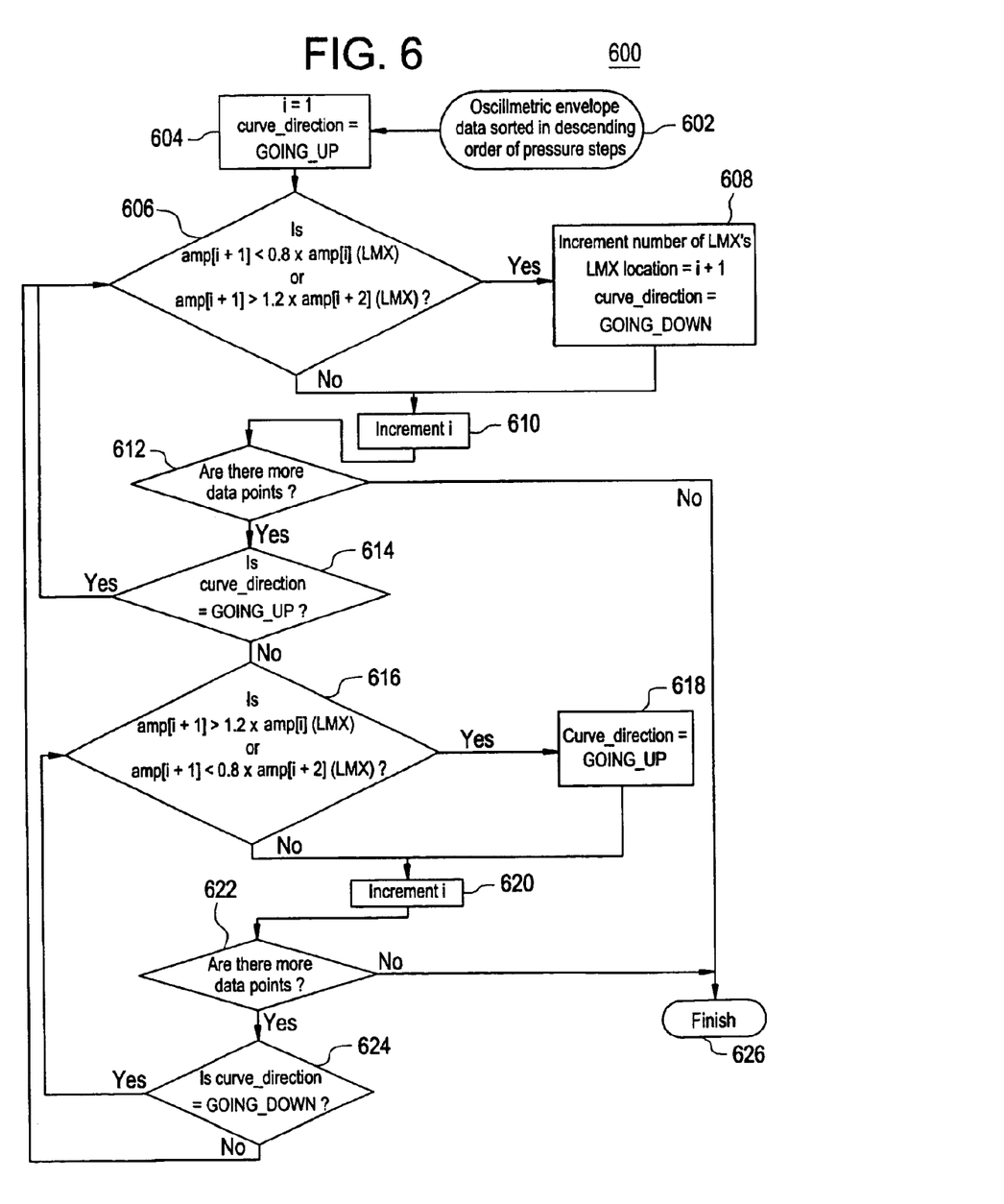
FIG. 6 is a flow chart of the process of identifying a local minima or maxima in an oscillometric envelope according to an embodiment of the present invention.

FIG. 6 shows a process for identifying a local extreme (i.e., a local maxima or local minima) that is about 20% higher or lower than a prior consecutive point. This process functions as a way to identify potential artifacts and thereby eliminate them from data. First, the oscillometric envelope data is sorted in descending order of pressure steps at step 602. Next, two consecutive points are taken at step 604 where "i" represents the first data point in the sorted data. For example, points A1 and A2 on FIG. 1B represent two consecutive points that can be used. Whether or not the second point is 20% lower or higher than the prior consecutive point is determined at step 606 on FIG. 6. More specifically, for a segment of the envelope that is generally going up in complex amplitude as the cuff pressure steps decrease, step 606 determines whether $$\text{amp}[i+1] < (0.8 \times \text{amp}[i])$$

for local minima, or it is determined whether $$\text{amp}[i+1] > (1.2 \times \text{amp}[i+2])$$

for local maxima. For these determinations, amp[i] is simply the mm of Hg as a measure of amplitude for a particular point on the oscillometric envelope. Thus, amp[i+1] and amp[i+2] are amplitudes for subsequent points along the envelope. If the conditions of step 606 are satisfied, the data point amp[i+1] is considered a local extreme at step 608. Step 610 takes the next data point after either finding a local extreme at step 608 or not meeting any conditions at step 606. From the next data point, the process determines whether there are any more data points at step 612. If there are more data points, the process determines whether the curve direction is generally upward. If so, the process returns back to step 606 to analyze the next data points relative to one another. If there are not any more data points at step 612, the process is finished at step 626. If the curve direction is not generally upward, but is instead downward, the determination is made whether $$\text{amp}[i+1] > (1.2 \times \text{amp}[i])$$

for local maxima or $$\text{amp}[i+1] < (0.8 \times \text{amp}[i+2])$$

for local minima at step 616. If these conditions of step 616 are met, the curve direction is changed at step 618 for detection of other local extremes. If the conditions of step 616 are not met, the analysis proceeds to the next amplitude point on the envelope at step 620. At step 622, it is determined whether there are any more data points. If so, the process determines whether the curve direction is generally downward at step 624. If the direction is downward, the process returns to step 616. If the direction is not downward, the process returns to step 606. If there are no more data points at step 622, the process of FIG. 6 for determining the number of local extremes is complete. The number of local extremes are then used to remove artifact as described in FIG. 2.

Figure 7:
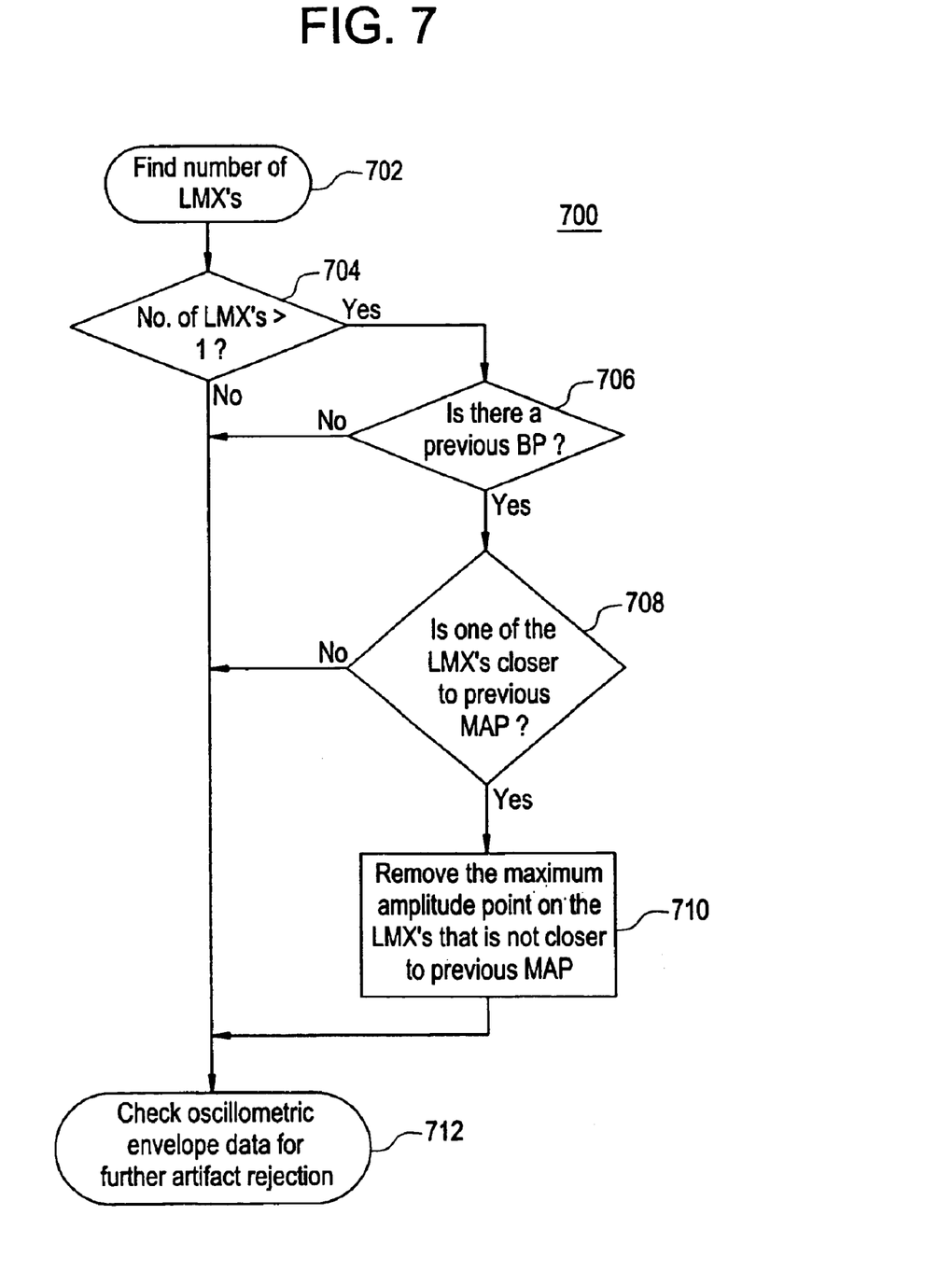
FIG. 7 is a flow chart of the process of using previous blood pressure measurements to identify false local maximas according to an embodiment of the present invention.

FIG. 7 shows a process for identifying a false local maxima based on a previous blood pressure and MAP. First, the number of local maxima are determined at step 702 (using the process described in FIG. 6). Once this is determined, the process determines whether the number of local maxima is greater than one at step 704. If so, the process determines whether there is a previously known blood pressure from within a predetermined time period (e.g., 16 minutes) at step 706. Of course, the length of time used in step 706 can vary according to different time periods that are customary in the field. If there is a previously known blood pressure from step 706, the process determines whether the cuff pressure corresponding to one of the local maxima is closer to the previous MAP at step 708. If so, the maximum amplitude point on the local maxima that has the largest difference in value with the previous MAP ((cuff pressure at local maxima−previous MAP) is the largest) is removed at step 710. If the conditions of steps 706 or 708 are not met, the process checks oscillometric envelope data for further artifact rejection at step 712. In addition, after removing one of the local maxima at step 710, the process proceeds to step 712.

Figure 8:
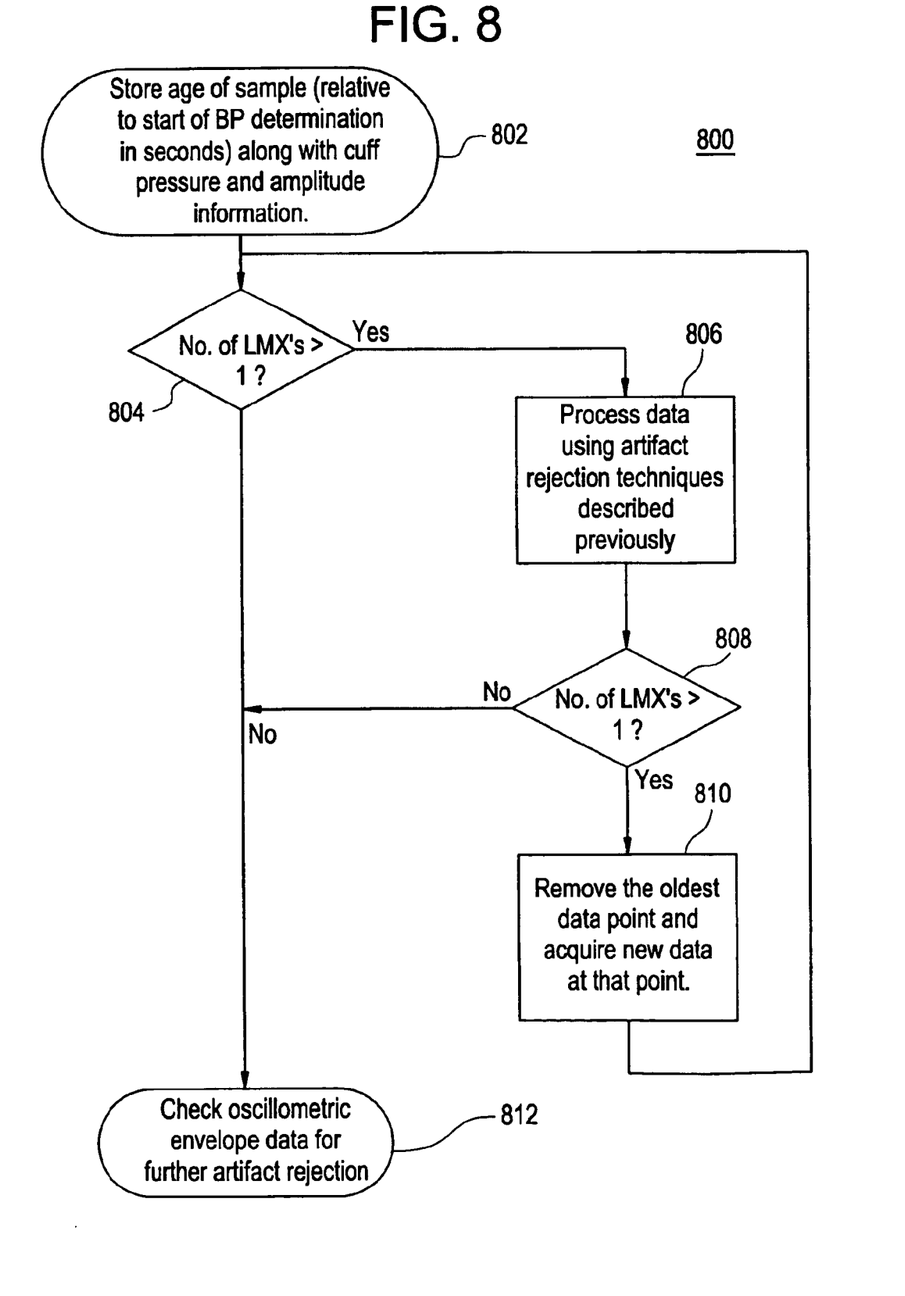
FIG. 8 is a flow chart of the process of using the age of the data sample to reject noise from an oscillometric envelope according to an embodiment of the present invention.

FIG. 8 shows a process of eliminating the oldest data point from the oscillometric envelope data. In other words, FIG. 8 shows a way to use the age of the data sample to reject noise from data. The age of a sample relative to the start of a blood pressure determination (e.g., acquisition time) along with cuff pressure and amplitude information are stored at step 802. The process includes determining whether the number of local maxima is greater than one at step 804. If so, the data is processed using the artifact rejection techniques explained in connection with the descriptions of the other figures at step 806. The process then includes determining whether the number of local maxima is greater than one at step 808. If so, the oldest data point is removed and a new data point is acquired at that point at step 810. The process then reverts back to step 804 to determine whether the number of local maxima is greater than one. If the number of local maxima is not greater than one at step 804, 808, the oscillometric envelope data is checked for further artifact rejection at step 812. It should be noted that each of the steps described above are applicable to local minima as well as local maxima.

Figure 9:
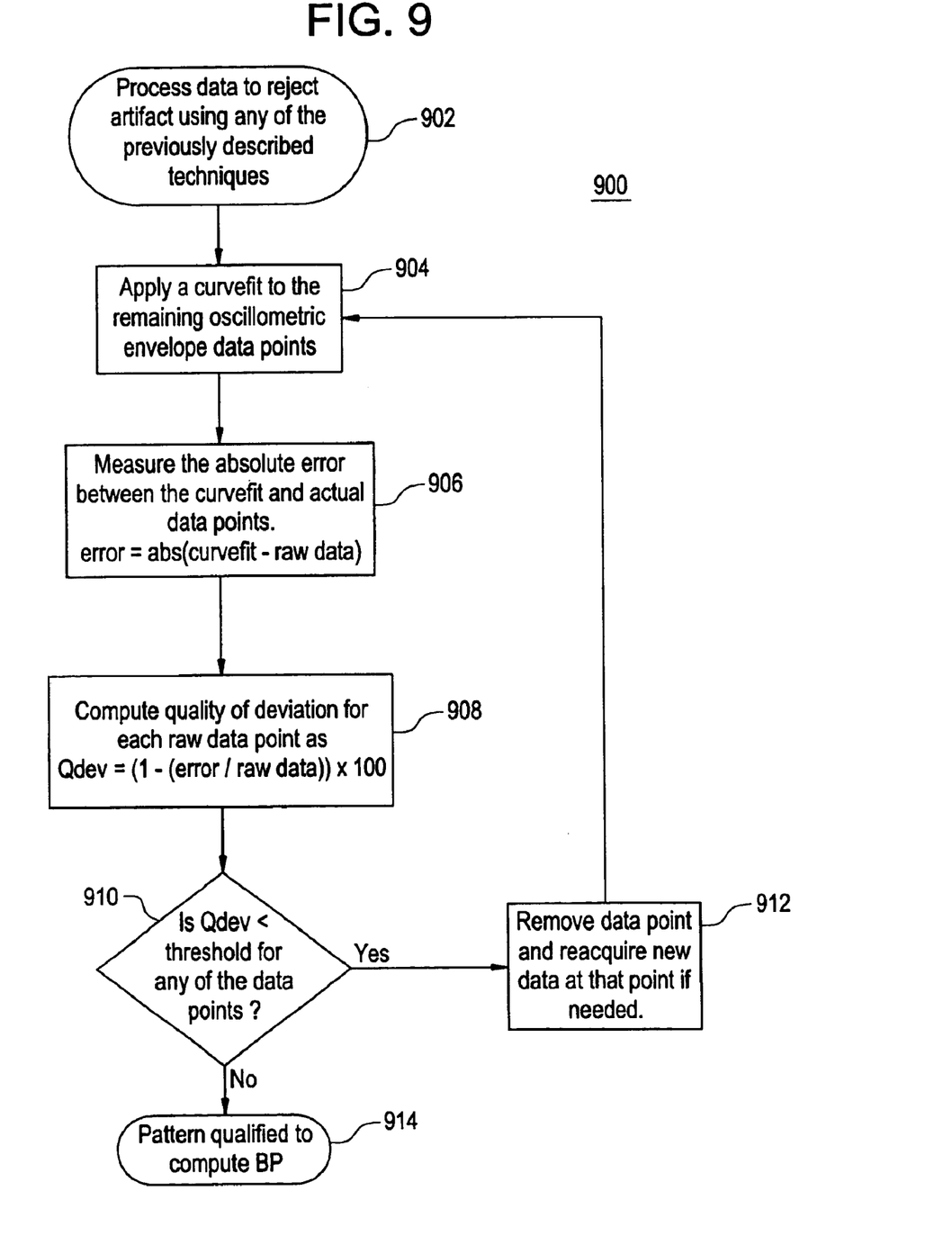
FIG. 9 is a flow chart of the process of using error from curve fitting techniques to reject noise from an oscillometric envelope according to an embodiment of the present invention.

FIG. 9 shows a process for using error from curve fitting techniques to reject noise from an oscillometric envelope. Data is processed to reject artifacts according to any of the techniques described with the other figures at step 902. Once these procedures are completed, a curvefit is applied to the remaining oscillometric envelope data points at step 904. The curve may be computed using a variety of known techniques. One example of such a technique of computationally fitting a curve to an oscillometric envelope is disclosed in U.S. Pat. No. 5,704,362 to Hersh et al. The absolute error is then measured between the curvefit and the actual data points at step 906 according to the following equation:

$$error = |curvefit - rawdata|$$

where error is absolute error, curvefit is an amplitude derived from a curvefit of envelope data at a same pressure that corresponds to the raw data, and raw data are measured envelope data points. Next, the quality of deviation is computed for each raw data point at step 908. In computing the quality of deviation (Qdev), the following equation may be used:

$$Qdev = \left(1 - \left(\frac{error}{raw\ complex\ amplitude}\right)\right) \times 100$$

where Qdev is quality of deviation, error is error previously determined, and raw complex amplitude are data point(s) used. Whether Qdev is less than the threshold for any of the data points is determined at step 910. If so, the data point is removed and a new data point is reacquired for that point (if necessary) at step 912. Then the process returns to step 904 to apply a curvefit to the remaining oscillometric envelope data points. If Qdev is less than the threshold for all of the data points at step 910, the pattern is qualified to compute blood pressure at step 914. It is important to note that the threshold can be any number of different values as required for a particular situation or as is generally accepted within the art.

While the embodiments and application of the invention illustrated in the figures and described above are presently preferred, it should be understood that these embodiments are offered by way of example only. Accordingly, the present invention is not limited to a particular embodiment, but extends to various modifications that nevertheless fall within the scope of this application.

What is claimed is:

1. A method of rejecting artifacts in oscillometric envelope blood pressure data comprising:

evaluating conformance of the oscillometric envelope blood pressure data with a predetermined expected pattern, wherein evaluating conformance of the oscillometric envelope blood pressure data comprises locating a plurality of local extremes, including a first local extreme;

excluding one or more data points of the oscillometric envelope blood pressure data based on non-conformance with the expected pattern, wherein excluding one or more data points of the oscillometric envelope blood pressure data comprises removing the first local extreme;

determining whether the blood pressure data includes a second local extreme; and adding the first local extreme that was removed and excluding the second local extreme.

2. The method of claim 1, wherein evaluating conformance of the oscillometric envelope blood pressure data comprises identifying a minimum number of points on a systolic side of the oscillometric envelope blood pressure data that are below an allowed threshold.

3. The method of claim 2, wherein excluding one or more data points of the oscillometric envelope blood pressure data comprises removing a maximum amplitude point if a predetermined number of the identified points on the systolic side of the oscillometric envelope blood pressure data are below the allowed threshold.

4. The method of claim 1, wherein excluding one or more data points of the oscillometric envelope blood pressure data comprises removing data points along a curved portion of an oscillometric envelope that do not have a value within an accepted range of tolerance.

5. The method of claim 1, wherein the accepted range of tolerance comprises about 80% to about 120% of an immediately consecutive data point.

6. The method of claim 1, wherein evaluating conformance of the oscillometric envelope blood pressure data comprises arranging the oscillometric envelope blood pressure data in descending order of pressure steps.

7. The method of claim 1, wherein evaluating conformance of the oscillometric envelope blood pressure data comprises sorting data with respect to complex amplitudes, thereby creating a systolic side and a diastolic side of the oscillometric envelope blood pressure data.

8. A method of rejecting artifacts in oscillometric envelope blood pressure data comprising:

evaluating conformance of the oscillometric envelope blood pressure data with a predetermined expected pattern, wherein evaluating conformance of the oscillometric envelope blood pressure data comprises sorting data with respect to complex amplitudes, thereby creating a systolic side and a diastolic side of the oscillometric envelope blood pressure data;

selecting at least a minimum number of data points on the systolic side and the diastolic side that exceed an allowed threshold, and removing all other data points; and excluding one or more data points of the oscillometric envelope blood pressure data based on non-conformance with the expected pattern.

9. The method of claim 8, further comprising identifying and removing side tails on at least one of the systolic side and diastolic side.

10. An apparatus for measuring blood pressure comprising:

an inflatable cuff;

a pressurizing apparatus coupled to the cuff for selectively applying pressure by inflating or deflating the cuff;

a cuff pressure sensor coupled to the cuff for sensing cuff pressure and blood pressure oscillations; and a programmed control device having functions that include:

controlling the pressure cuff and pressurizing apparatus;

evaluating conformance of the blood pressure oscillations with a predetermined expected pattern, wherein evaluating conformance of the oscillometric envelope blood pressure data comprises locating a plurality of local extremes, including a first local extreme;

excluding one or more data points of the blood pressure oscillations based on non-conformance with the expected pattern, wherein excluding one or more data points of the oscillometric envelope blood pressure data comprises removing the first local extreme;

determining whether the blood pressure data includes a second local extreme; and adding the first local extreme that was removed and removing the second local extreme.

11. A system for rejecting artifacts in oscillometric envelope blood pressure data comprising:

means for evaluating conformance of the oscillometric envelope blood pressure data with a predetermined expected pattern, wherein the evaluating means are configured to locate a plurality of local extremes, including a first local extreme;

means for excluding one or more data points of the oscillometric envelope blood pressure data based on non-conformance with the expected pattern, wherein the excluding means are configured to remove the first local extreme; and means for determining whether the blood pressure data includes a second local extreme; and means for adding the first local extreme that was removed and means for removing the second local extreme.

* * * * *